United States Patent [19]

Souma

[11] Patent Number: 5,197,478
[45] Date of Patent: Mar. 30, 1993

[54] AUTOMATIC SPHYGMOMANOMETER FOR PREDICTIVELY MEASURING PRESSURE BY SAMPLING PULSE WAVE SIGNAL

[75] Inventor: Takahiro Souma, Fuji, Japan

[73] Assignee: Terumo Kabushiki Kaisha, Tokyo, Japan

[21] Appl. No.: 879,695

[22] Filed: May 5, 1992

Related U.S. Application Data

[63] Continuation of Ser. No. 362,445, May 18, 1989, abandoned.

[30] Foreign Application Priority Data

Nov. 19, 1986 [JP] Japan .................... 61-274087

[51] Int. Cl.$^5$ .................................. A61B 5/02
[52] U.S. Cl. ........................ 128/681; 128/682
[58] Field of Search .................. 128/677–683

[56] References Cited

U.S. PATENT DOCUMENTS

| | | | |
|---|---|---|---|
| 4,461,266 | 7/1984 | Hood, Jr. et al. ........... | 128/677 |
| 4,699,152 | 10/1987 | Link ........................... | 128/677 |
| 4,776,344 | 10/1988 | Shirasaki .................... | 128/681 |
| 4,830,019 | 5/1989 | Shirasaki et al. .......... | 128/680 |

FOREIGN PATENT DOCUMENTS

| | | |
|---|---|---|
| 3424535 | 1/1986 | Fed. Rep. of Germany ...... 128/681 |
| 60-40038 | 3/1985 | Japan . |
| 61-79442 | 4/1986 | Japan . |
| 2165052 | 4/1986 | United Kingdom . |

OTHER PUBLICATIONS

European Search Report completed Nov. 23, 1989 in The Hague, by Examiner A. Ferrigno, citing 5 references.

*Primary Examiner*—William E. Kamm
*Assistant Examiner*—Robert L. Nasser, Jr.
*Attorney, Agent, or Firm*—Staas & Halsey

[57] ABSTRACT

An automatic sphygmomanometer of this invention is arranged to predict, on the basis of the relationship between cuff pressure and the amplitude of a pulse wave, maximal and minimal blood pressures while the cuff pressure is being increased. This automatic sphygmomanometer is capable of minimizing the discomfort inflicted upon a subject by increasing or reducing the cuff pressure to the neighborhood of a predicted maximal or minimal blood pressure at a relative high rate. Concretely, the pressure in the cuff is increased at a relatively high pressure-increasing rate to a level immediately below the predicted maximal blood pressure and, thereafter, the pressure-increasing rate is reduced to a rate suitable for measurement. The maximal blood pressure is in turn measured. When the minimal blood pressure is to be measured, as soon as the maximal blood pressure has been measured, the cuff pressure is rapidly reduced to a level immediately above the predicted minimal blood pressure and, then, the pressure-reducing rate is reduced. The minimal blood pressure is measured under the condition of this reduced rate. Accordingly, it is possible to minimize the discomfort inflicted upon the subject due to pressure and a lengthy operation. Moreover, this invention eliminates the awkward operation of setting a pressure which is approximately 30 mmHg higher than the expected maximal blood pressure.

13 Claims, 6 Drawing Sheets

AUTOMATIC SPHYGMOMANOMETER FOR PREDICTIVELY MEASURING PRESSURE BY SAMPLING PULSE WAVE SIGNAL

This application is a continuation of application Ser. No. 07/362,445, filed May 18, 1989, now abandoned.

DESCRIPTION

1. Technical Field

The present invention relates to an automatic sphygmomanometer and, more particularly, to an automatic sphygmomanometer arranged to automatically process a sequence of blood pressure measurement operations.

2. Background Art

Conventional sphygmomanometers of this type are commonly arranged first to increase the air pressure in the air back incorporated in an arm band (hereinafter referred to simply as the "arm band") to a pressure which is approximately 30 mmHg higher than the expected maximal blood pressure of a subject (the maximal blood pressure expected by a person who conducts the measurement of blood pressure) and then to measure the blood pressure while reducing that air pressure at a rate as slow as 3-4 mmHg/second.

As is known, it is customary to preset the pressure corresponding to the expected maximal blood pressure plus 30 mmHg by means of a switch having, for example, five settings.

Blood pressure measurement utilizing such a sphygmomanometer will be described in detail below.

First, the instant that Korotkoff sounds initially appear while the pressure in the arm band is being reduced from its fully increased state or the time instant that small variations in the pressure in the arm band increase is detected, and the air pressure in the arm band at that instant is measured to obtain the maximal blood pressure. Thereafter, the instant that the Korotkoff sounds disappear while the pressure in the arm band is being gradually reduced or the instant that small variations in the pressure in the arm band abruptly decreases is detected, and the air pressure in the arm band at that instant is measured to obtain the minimal blood pressure.

However, since the pressure in the arm band is slowly reduced from a pressure higher than the expected maximal blood pressure to the minimal blood pressure, it has been impossible to avoid the problem that the discomfort inflicted upon an arm of the subject becomes serious.

Moreover, it has been necessary to involve the awkward operation of setting a pressure which is approximately 30 mmHg higher than the pressure expected as the maximal blood pressure.

DISCLOSURE OF THE INVENTION

In view of the foregoing difficulties with the prior art, it is an object of the present invention to provide an automatic sphygmomanometer capable of measuring maximal blood pressure in a short time without increasing the pressure in the arm band to a level substantially higher than the maximal blood pressure.

To achieve this object, an automatic sphygmomanometer according to the present invention is provided with pressure detecting means for detecting cuff pressure, first pressure increasing means for increasing the cuff pressure at a high pressure-increasing rate, pulse-wave signal detecting means for detecting the amplitude of the pulse-wave signal of a subject while the first pressure-increasing means is increasing the cuff pressure, maximal blood pressure predicting means for predicting a maximal blood pressure from the detected amplitude of the pulse-wave signal, second pressure-increasing means for increasing the cuff pressure at a rate lower than the pressure-increasing rate of the first pressure-increasing means when the pressure detecting means determines that the cuff pressure has been increased to a predetermined level below the predicted maximal blood pressure, measuring means for measuring the maximal blood pressure while the second pressure-increasing means is increasing the cuff pressure, and de-energizing means for de-energizing the second pressure-increasing means after the measuring means has measured the maximal blood pressure, in order to prepare to measure a minimal blood pressure.

In accordance with one preferred form of the present invention, the first pressure-increasing means is activated after the cuff pressure has reached approximately 20 mmHg, and it is preferable for the cuff pressure to be rapidly increased until the cuff pressure reaches approximately 20 mmHg.

In accordance with this preferred form of the present invention, it is also preferable for the pressure-increasing rate of the first pressure-increasing means to be approximately 50 mmHg/7 seconds.

In accordance with the preferred form of the present invention, it is also preferable for the predicting means to predict the maximal blood pressure by utilizing the proportion of the amplitude of the pulse-wave signal to the maximum amplitude thereof.

In accordance with the preferred form of the present invention, it is also preferable for the second pressure-increasing means to be energized when the pressure detecting means detects a pressure corresponding to the maximum amplitude of the pulse-wave signal.

Further, in accordance with the preferred form of the present invention, it is preferable for the pressure-increasing rate of the second pressure-increasing means to be approximately 50 mmHg/12 seconds.

Moreover, in accordance with the preferred form of the present invention, it is preferable for a limiter to be provided for preventing the cuff pressure from exceeding a predetermined pressure.

It is another object of the present invention to provide an automatic sphygmomanometer with which it is possible to reduce the time required from the beginning to the end of measurement of blood pressure and which is capable of measuring blood pressure without increasing cuff pressure to a level substantially higher than the maximal blood pressure.

To achieve this object, an automatic sphygmomanometer according to the present invention is provided with pressure detecting means for detecting cuff pressure, first pressure-increasing means for increasing the cuff pressure at a high pressure-increasing rate, pulse-wave signal detecting means for detecting the amplitude of the pulse-wave signal of a subject while the first pressure-increasing means is increasing the cuff pressure, predicting means for predicting maximal and minimal blood pressures from the detected amplitude of the pulse-wave signal, second pressure-increasing means for increasing the cuff pressure at a rate lower than the pressure-increasing rate of the first pressure-increasing means when the pressure detecting means detects an increase in the cuff pressure to a predetermined level below the predicted maximal blood pressure, maximal blood pressure measuring means for measuring the maximal blood pressure while the second pressure-increasing means is increasing the cuff pressure, first pressure-reducing means for reducing the cuff pressure at a high pressure-reducing rate after the maximal blood pressure has been measured, second pressure-reducing means for reducing the cuff pressure at a rate lower than the pressure reducing rate of the first pressure-reducing means when the pressure detecting means detects a reduction in the cuff pressure to a predetermined level immediately above the predicted minimal blood pressure, and minimal blood pressure measuring means for measuring the minimal blood pressure while the second pressure reducing means is reducing the cuff pressure.

In accordance with a preferred form of the present invention, the first pressure-increasing means is activated after the cuff pressure has reached approximately 20 mmHg, and it is preferred for the cuff pressure to be rapidly increased until the cuff pressure reaches approximately 20 mmHg.

In accordance with the preferred form of the present invention, it is also preferable for the pressure-increasing rate of the first pressure-increasing means to be approximately 50 mmHg/7 seconds.

In accordance with the preferred form of the present invention, it is also preferable for the predicting means to predict the maximal and minimal blood pressures by utilizing the proportion of the amplitude of the pulse-wave signal to the maximum amplitude thereof.

In accordance with the preferred form of the present invention, it is also preferable for the second pressure-increasing means to be energized when the pressure detecting means detects a pressure corresponding to the maximum amplitude of the pulse-wave signal.

In accordance with the preferred form of the present invention, it is also preferable for the pressure-increasing rate of the second pressure-increasing means to be approximately 50 mmHg/12 seconds.

In accordance with the preferred form of the present invention, it is also preferable for the first pressure-reducing means to be energized by opening an exhaust valve.

In accordance with the preferred form of the present invention, it is also preferable for the second pressure-reducing means to be energized when the pressure detecting means determines that the cuff pressure has become approximately equal to 10 mmHg plus a pressure corresponding to the maximum amplitude of the pulse-wave signal.

In accordance with the preferred form of the present invention, it is also preferable for the pressure reducing rate of the second pressure reducing means to be approximately 50 mmHg/12 seconds.

Moreover, in accordance with the preferred form of the present invention, it is preferable for cuff-charged air to be rapidly exhausted after the measuring means has measured the minimal blood pressure.

Further, in accordance with the preferred form of the present invention, it is preferable for a limiter to be provided for preventing the cuff pressure from exceeding a predetermined pressure.

BEST MODE FOR CARRYING OUT THE INVENTION

An embodiment of the present invention will be described in detail below with reference to the accompanying drawings.

Figure 1A:
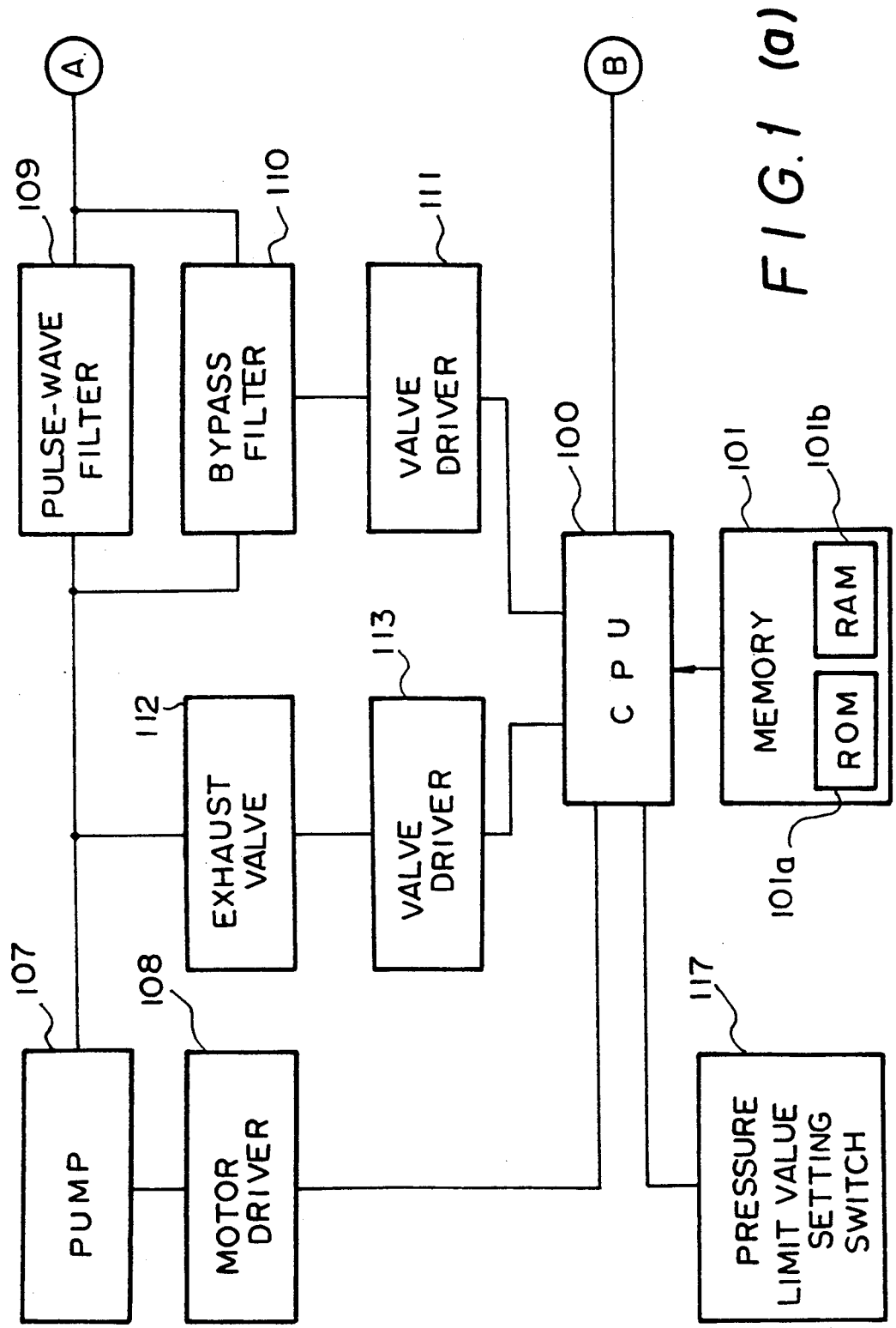
FIGS. 1(a) and 1(b) are block diagrams showing an embodiment of an automatic sphygmomanometer according to the present invention.
Figure 1:
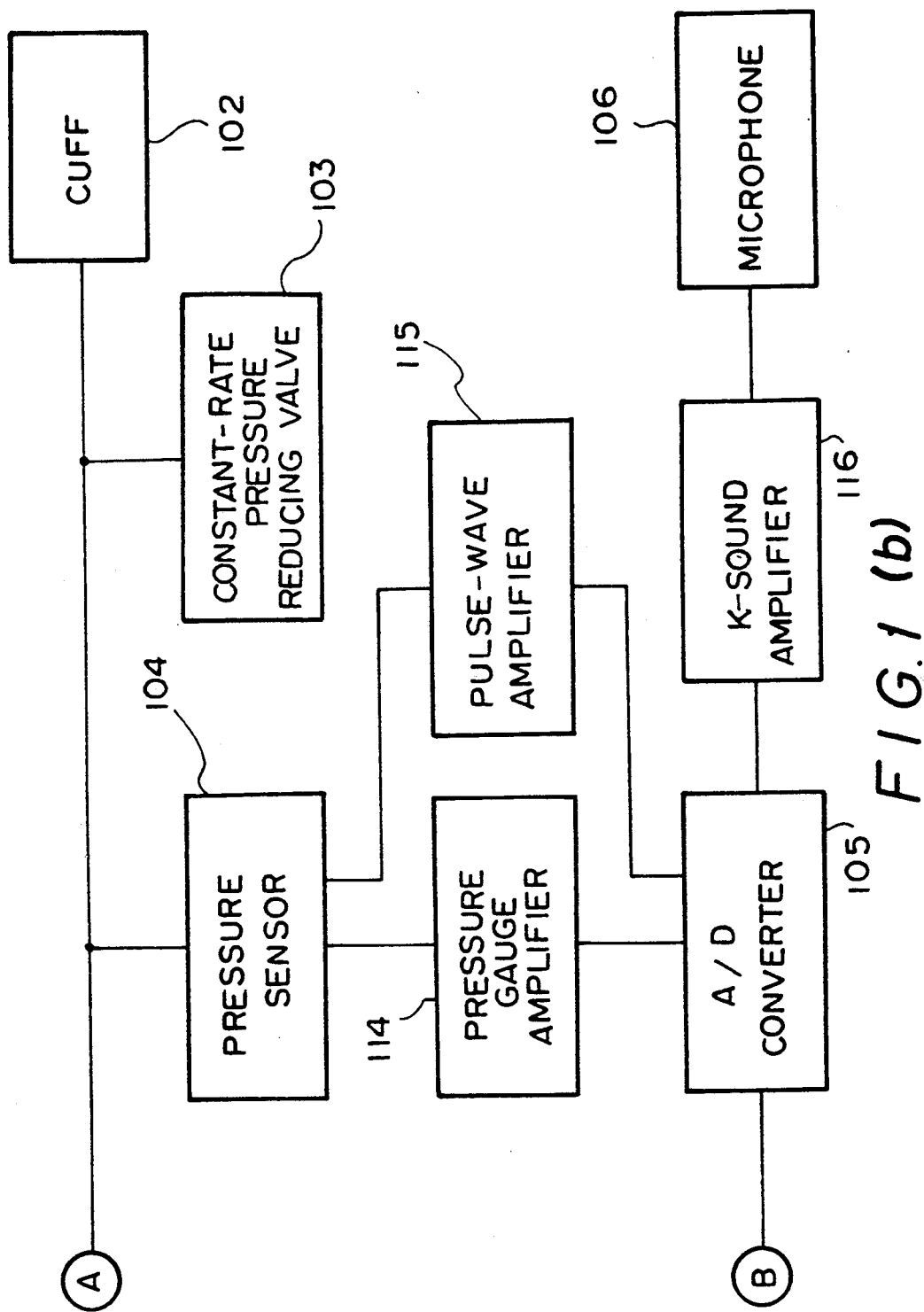

FIGS. 1(a) and 1(b) are block diagrams which show the basic construction of an embodiment of an automatic sphygmomanometer according to the present invention.

In these figures, a microprocessor (hereinafter referred to simply as "CPU") for controlling the whole apparatus is denoted at 100, and CPU 100 is arranged to operate in accordance with the process procedure (program) shown in the flowchart of FIGS. 4(a) to 4(c), which will be explained later. This process procedure is stored as a program in ROM 101a incorporated in memory 101. Memory 101 further includes RAM 101b which is used as a work area for CPU 100 or for storage of various types of data. A cuff (arm band) is denoted at 102, and a constant-rate pressure reducing valve 103 is provided in this cuff 102 so that air is exhausted at a constant rate. Reference numeral 104 denotes a pressure sensor for detecting the air pressure within the cuff 102 to output the detection value as an analog value. This output is amplified by a pressure gauge amplifier 114, while the pulse-wave component contained in the output is amplified by a pulse-wave amplifier 115. The analog outputs of the respective amplifiers 114 and 115 are converted into digital values by an A/D converter 105. A microphone 106 is provided in the cuff 102, and serves to detect Korotkoff sounds (hereinafter referred to as the "K sounds") with the cuff 102 placed around an arm of the subject. The K sounds detected by the microphone 106 are amplified by a K sound amplifier 116 and fed to the A/D converter 105 described above. A pump for pumping air into the cuff 102 is denoted by 107, and is driven by a motor driver 108. Reference numeral 109 denotes a pulse-wave filter for shaping the flow of the air discharged from the pump 107 when the air is being charged into the cuff 102. Reference numerals 111 and 113 denote valve drivers for opening and closing a bypass filter 110 and an exhaust valve 112, respectively. A pressure limit value setting switch is denoted by 117, and the pressure limit value set by this switch 117 is fed to CPU 100. This arrangement makes it possible to prevent pressure above this limit value from being applied to the subject. After a pulse-wave peak point has been detected, a predicted value plus 30 mmHg is employed as the pressure limit value. This predicted value is obtained by predicting a maximal blood pressure by using the following equation on the basis of a minimal blood pressure derived from a pulse wave detected during a pressure-increasing process or a minimal blood pressure derived from the K sounds and an average blood pressure corresponding to the pulse-wave peak point. Alternatively, it is also possible to employ, as the pressure limit value, the blood pressure existing when the amplitude of a pulse wave reaches 5-30% of the pulse-wave amplitude of the average blood pressure corresponding to the pulse-wave peak point.

$$\begin{aligned}\text{Expected maximal}\\ \text{blood pressure}\end{aligned} = \begin{aligned}\text{average blood}\\ \text{pressure}\end{aligned} \times 1.06 +$$

$$2 \times \left(\begin{aligned}\text{average blood}\\ \text{pressure}\end{aligned} \times 1.05 - \begin{aligned}\text{minimal blood}\\ \text{pressure}\end{aligned}\right)$$

In other words, while CPU 100 is increasing the pressure in the cuff 102 during measurement of blood pressure, if CPU 100 determines that the cuff pressure has reached the expected maximal blood pressure, then CPU 100 causes air to be exhausted from the cuff 102 in order to immediately stop the measurement.

The basic operation of the present sphygmomanometer having the above-described arrangement will be explained below.

As air is being fed into the cuff 102 by driving the pump 107 with the cuff (arm band) 102 placed around an arm of the subject, a pulse-wave signal is detected by the pressure sensor 104. This pulse wave is shown in electrical-signal form in FIG. 2. For the sake of simplifying the explanation, it is assumed that the cuff pressure is increased at a constant ratio.

Figure 2:
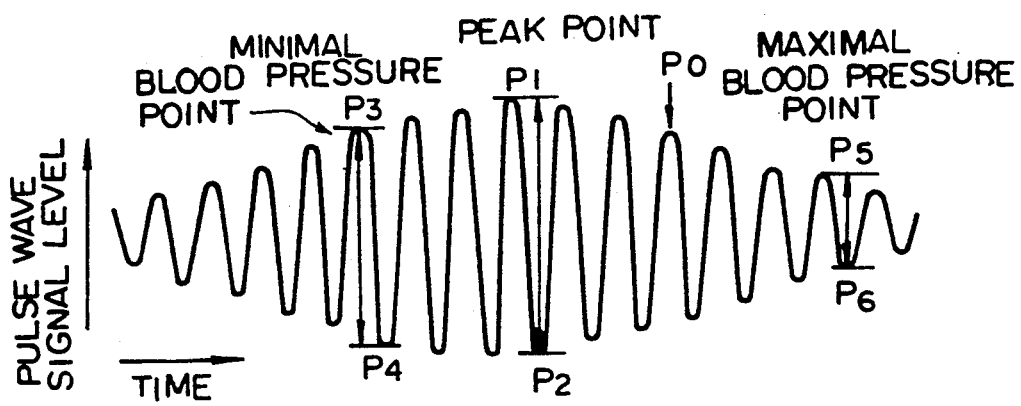
FIG. 2 is a graphic representation showing the relationship between time and the amplitude of a pulse-wave signal when the rate of pressure-increase is constant.

As the cuff pressure is increased, the amplitude of the pulse wave signal gradually increases, and after this amplitude passes a peak point (P1·P2), it gradually decays. In general, as shown in FIG. 2, if the peak point of the amplitude of the pulse wave and that amplitude can be detected, it is possible to predict the maximal and minimal blood pressures of the subject. In the present embodiment, it is predicted that the minimal blood pressure is present in the neighborhood of an amplitude (P3·P4) which corresponds to 80% of the amplitude of the peak position, that is, the peak point (P1·P2) and that the maximal blood pressure is present in the neighborhood of an amplitude (P5·P6) which corresponds to 50% of the amplitude of the peak point (P1·P2). Incidentally, the above noted numerical values, such as 80% and 50%, are not construed as restrictive values since they may vary, depending upon the construction of the hardware.

It will be understood from the foregoing that, when the maximal blood pressure is to be measured, the pressure within the cuff 102 may be increased at a relatively high rate up to the instant of time slightly beyond the time corresponding to the peak position of the pulse-wave signal. In the present embodiment, the maximal amplitude is utilized as a limit up to which the cuff pressure can be increased at this relatively high rate, and after the amplitude of the pulse-wave signal has reached the limit, the rate of pressure-increase is slowed down to initiate measurement of the maximal blood pressure. That is to say, the maximal blood pressure is measured while the cuff pressure is being increased. Accordingly, it is possible to measure the maximal blood pressure without the need to impose upon the arm of the subject a burden which is 30 mmHg greater than the expected maximal blood pressure as in the case of prior art sphygmomanometers. The above process procedure for measuring blood pressure will be described in greater detail with reference to the graph of FIG. 3 and the flowchart shown in FIGS. 4(a) to 4(c).

Figure 3:
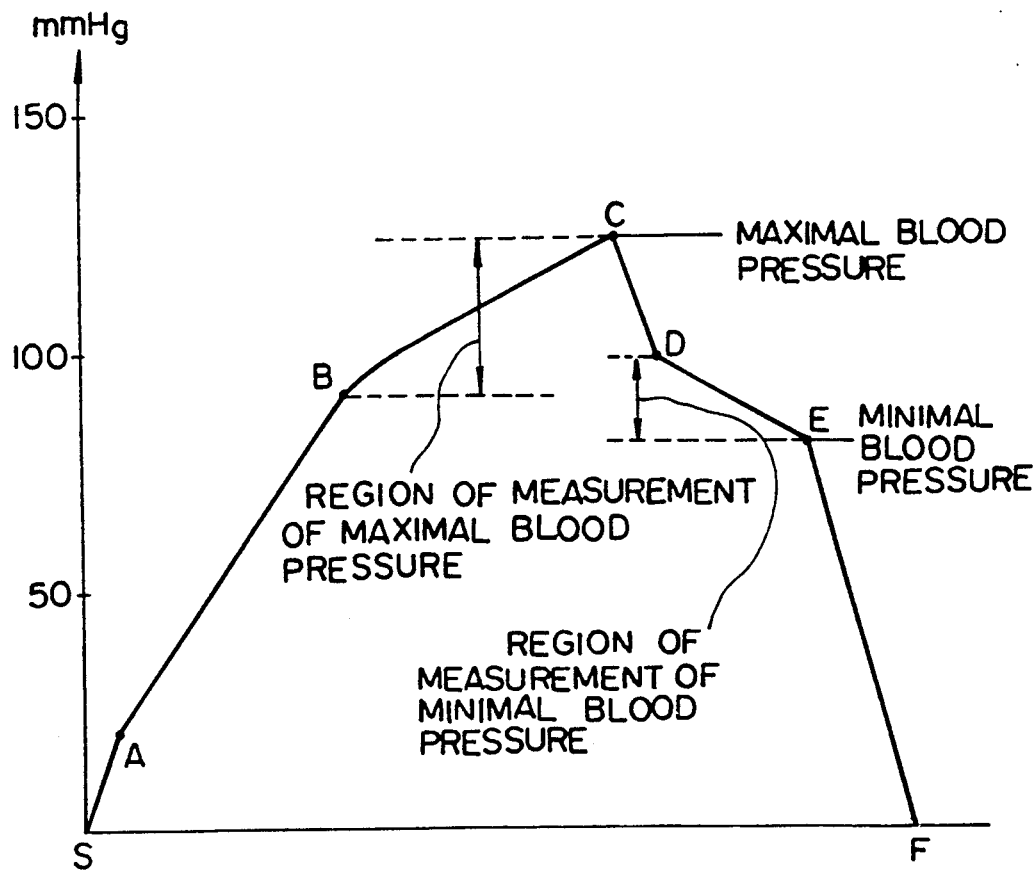
FIG. 3 is a graphic representation showing variations in the pressure in the cuff of the embodiment during measurement of blood pressure.

FIG. 3 is a graph which shows variations occurring in the pressure in the cuff 102 during a sequence of blood-pressure measuring steps conducted in accordance with the present embodiment, in which the vertical axis represents cuff pressure and the horizontal axis represents time.

Figure 4:
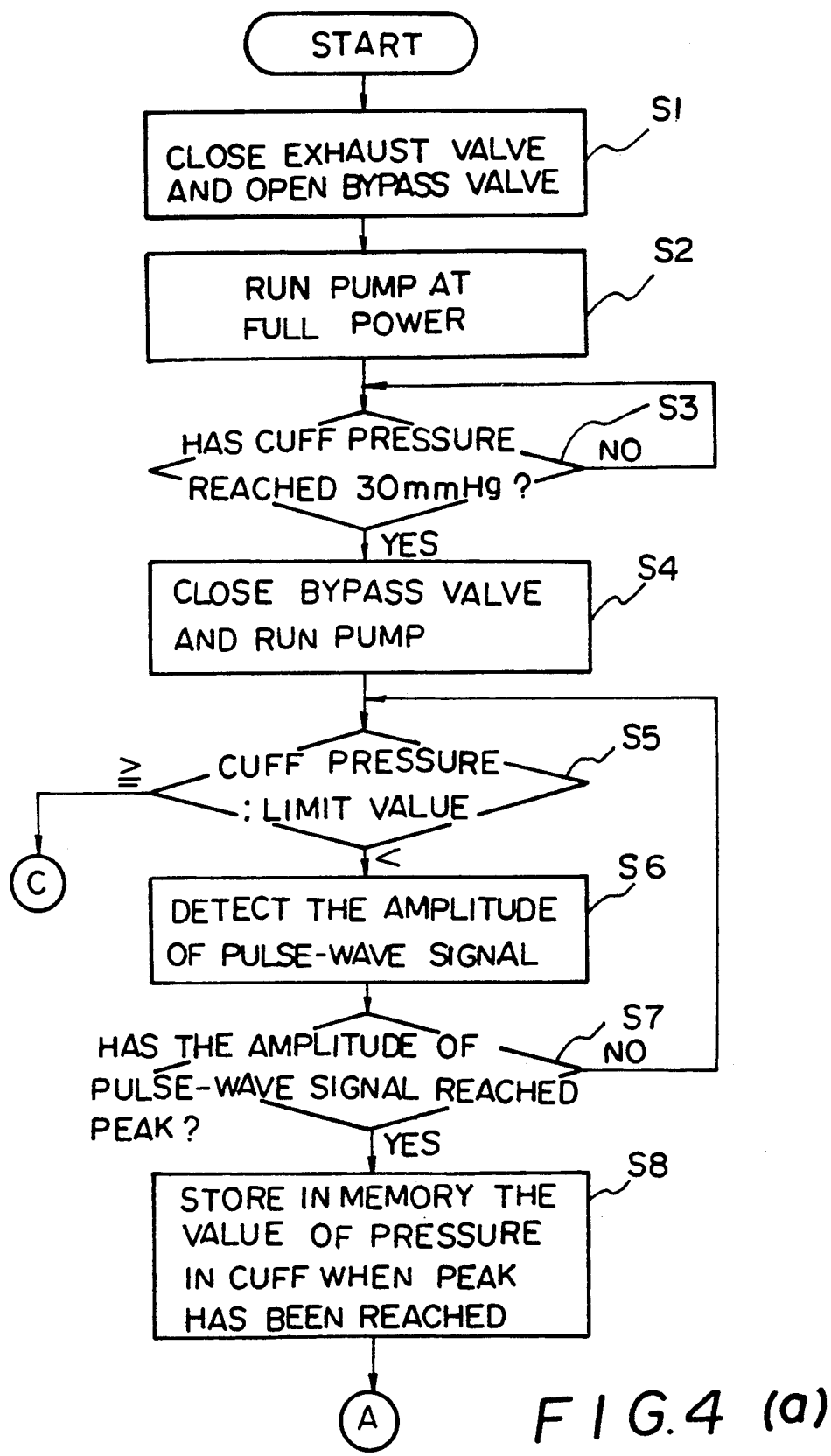
FIGS. 4(a) to 4(c) are flow charts which serve to illustrate a process procedure for measuring blood pressure in the present embodiment.
Figure 4:
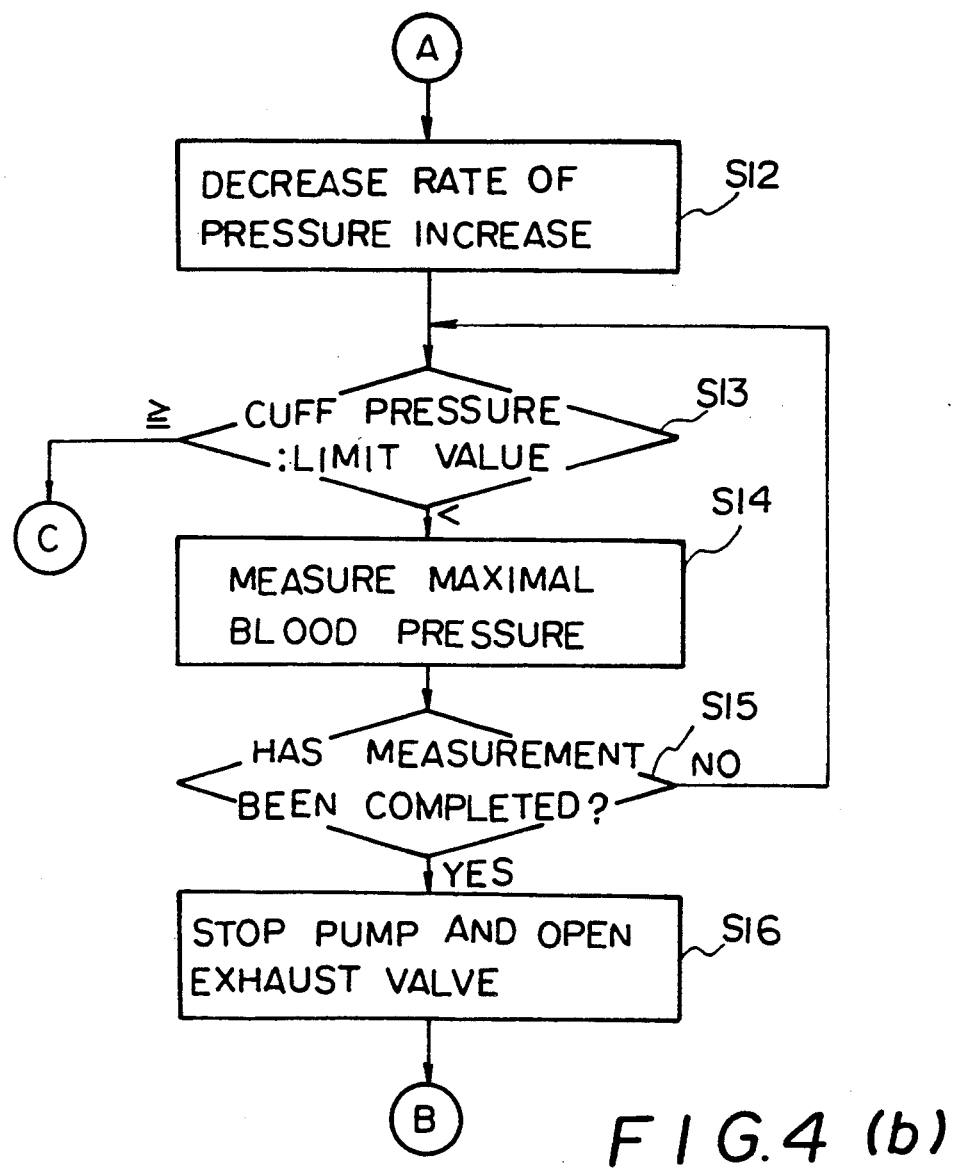
Figure 4:
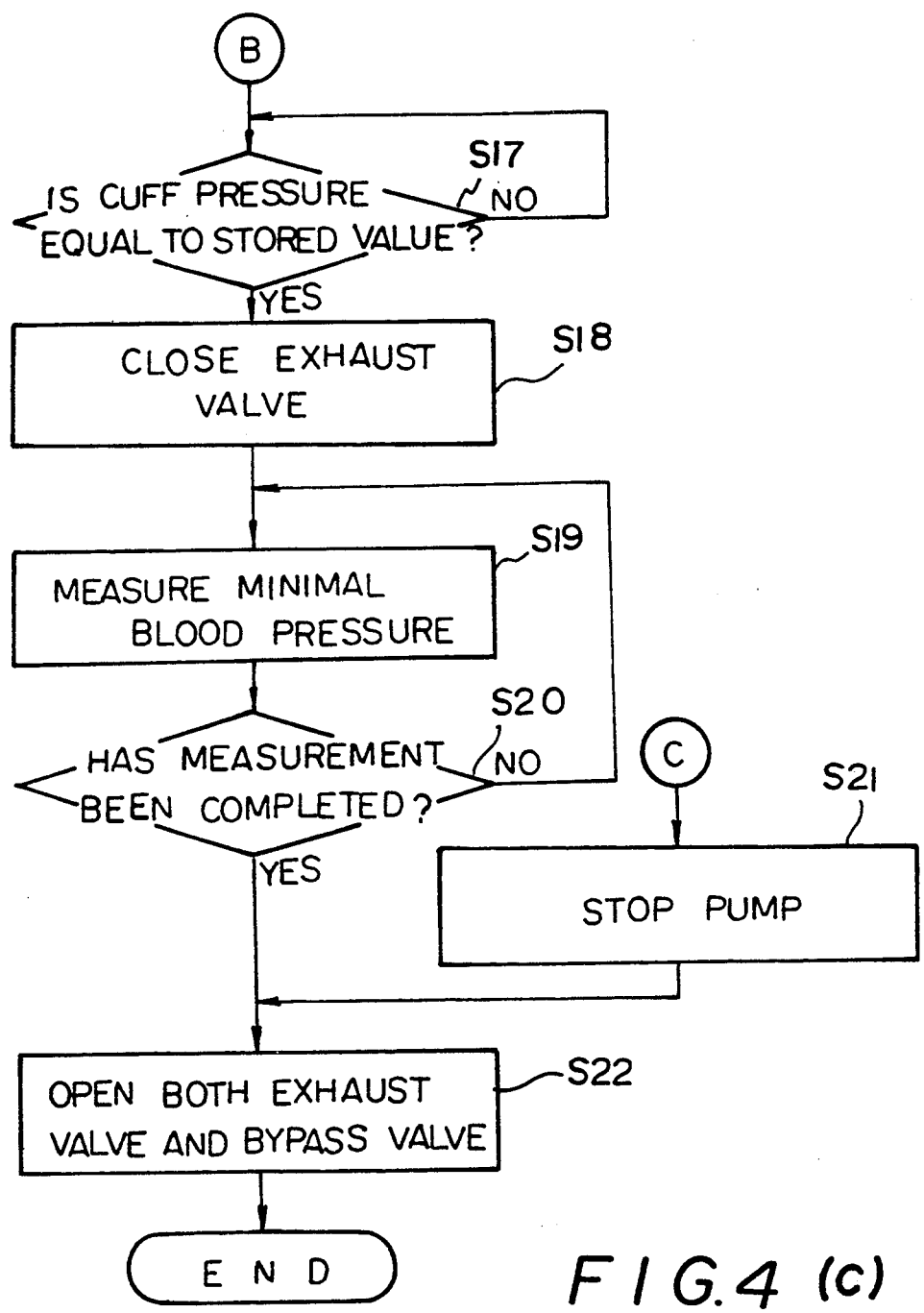

The process procedure shown in the flowchart of FIGS. 4(a) to 4(c) starts when a switch (not shown) for initiating measurement of blood pressure is actuated. This process procedure (program) is stored in ROM 101a in memory 101. In the following explanation, it is assumed that "150 mmHg" (hereinafter called the "limit value") is preset through the pressure limit value setting switch 117.

The period between S and A

When the switch (not shown) for initiating measurement of blood pressure is switched on, the process proceeds to Step S1, in which CPU 100 first energizes the valve driver 113 to close the exhaust valve 112 and, at the same time, energizes the valve driver 111 to open the bypass valve 110. Then, in Step S2, CPU 100 causes the pump 107 to run at full power and, in Step S3, waits for the pressure in the cuff 102 to reach 20 mmHg. It is thus possible to speed up the processing between points A and B, as will be described later.

The period between A and B

When the pressure in the cuff 102 reaches 20 mmHg, the process proceeds to Step S4, in which CPU 100 closes the bypass valve 110, actuates the pulse-wave filter 109, and sets the pump 107 to its normal running state, thereby setting the rate of pressure-increase to approximately 50 mmHg/7 seconds. The pressure in the cuff 102 gradually increases at this rate, and during this pressure-increase, CPU 100 executes the following processing.

First, in Step S5, CPU 100 compares the limit value with the pressure in the cuff 102. If it is determined that the cuff pressure is less than the limit value, the process proceeds to the next step S6, but if not, that is, if the pressure in the cuff 102 exceeds the limit value, the process jumps to Step S21, which will be described later.

In Step S6, the amplitude of a pulse-wave signal is detected through the A/D converter 105 and, in Step S7, whether the amplitude of the pulse-wave signal has reached its maximum is determined. If it is determined in Step S7 that the amplitude has not yet reached the maximum, the process returns to Step S5, in which a similar processing is repeated.

In practice, variations in the amplitude of the pulse-wave signal are sequentially measured, and the pulse-wave signal measured immediately before the magnitude of the amplitude starts to decrease is utilized as the pulse-wave signal of maximum amplitude.

After the pulse-wave signal of maximum amplitude has been measured, the process proceeds to Step S8, where the pressure in the cuff 102 and the amplitude of the pulse-wave signal which are obtained at this time are stored in RAM 101b of the memory 101.

In this manner, the pressure in the cuff 102 increases until the amplitude of the pulse-wave signal is detected at its maximum with the cuff pressure being lower than the limit value.

The period between B and C

If the amplitude of the pulse-wave signal reaches its being increased, it is determined that the cuff pressure has been increased up to the neighborhood of the maximal blood pressure, and measurement of the maximal blood pressure is initiated. In Step S12, the rate of pressure-increase is first reduced to 50 mmHg/12 seconds by controlling the pump 107. In the following step S13, a comparison between the cuff pressure and the limit value is made in a manner similar to that executed in Step S5. In Step S14, the measurement of the maximal blood pressure is initiated and, in Step S15, it is determined whether or not the measurement has been completed. If the answer is "NO", the above steps S13 to S15 are repeated until the measurement has been completed.

In practice, the maximal blood pressure is the pressure which exists one stroke before the instant that it becomes impossible to detect any K sound through the microphone 106 while the pressure in the cuff 102 is being increased at the aforesaid pressure-increasing rate (50 mmHg/12 seconds). Accordingly, strictly, point C in FIG. 3 corresponds to a pressure whose K sounds exceed the K sounds of the maximal blood pressure by two strokes.

Accordingly, since the maximal blood pressure is measured while the pressure in the cuff 102 is being increased, it is not necessary to increase the pressure in the cuff 102 to a value which is greater than the expected maximal blood pressure by approximately 30 mmHg as in the case of prior art apparatus. It is therefore possible to reduce the discomfort inflicted upon the arm of the subject. The measured maximal blood pressure is displayed on a display screen, output in printed form, or stored in a memory device or the like. However it is done, the method of processing measurement results is not to be limited by the present embodiment.

In addition, the maximal blood pressure is predicted from the amplitude of the pulse-wave signal. The pressure in the cuff 102 is increased at a high rate immediately before the predicted value and is thereafter increased at a rate at which the measurement can be made. It is therefore possible to measure the maximal blood pressure in a short time without causing a reduction in the accuracy of measurement of the maximal blood pressure.

The period between C and D

When the maximal blood pressure measurement has been completed, the process immediately proceeds to Step S16, in which the pressure in the cuff 102 is rapidly reduced by stopping the pump 107 and opening the exhaust valve 112. In Step S17, it is determined whether or not 10 mmHg plus the value stored in RAM 101b (the value of the pressure in the cuff 102 when the amplitude of the pulse-wave signal is at the maximum) is equal to the value of the pressure in the cuff 102 during the rapid reduction thereof. The process waits for these values to become equal. Incidentally, the value "10 mmHg" is selected by considering the response time of the apparatus, particularly that of a pressure system thereof.

The period between D and E

If it is determined that the pressure in the cuff 102 has become equal to the aforesaid value, that is, if it is determined that the cuff pressure has reached a level slightly higher than the minimal blood pressure, the exhaust valve 112 is immediately closed in Step S18. Thereafter, the pressure in the cuff 102 is reduced at a rate of approximately 50 mmHg/12 seconds by the action of the constant-rate pressure reducing valve 103.

Then, in steps S18 to S19, the minimal blood pressure is measured. In practice, the minimal blood pressure is obtained at instant that the K sounds from microphone 106 disappear while the pressure in the cuff 102 is being reduced.

As described above, in the case of the measurement of the minimal blood pressure as well, the pressure is reduced at a high rate to a pressure level immediately above the predicted minimal blood pressure. Thereafter, while the pressure is being decreased at a rate at which the measurement can be made, the minimal blood pressure is measured. It is therefore possible to achieve a reduction in time and, hence, reduce the irritation inflicted upon the arm of the subject due to a lengthy measurement period.

The period between E and F

After the maximal and minimal blood pressures have been measured, the exhaust value 112 and the bypass valve 110 are, in Step S22, fully opened to exhaust the air of the cuff 102 rapidly, thereby completing the measurement.

The case where the cuff pressure ≧ the limit value

If, in the processing described above, it is determined (Steps S5 and S13) that the pressure in the cuff 102 has been increased to a value higher than the limit value, the operation of a pressure-increasing pump is first stopped in Step S21 to rapidly exhaust, in Step S22, the air pumped into the cuff 102, thereby preventing the cuff pressure from increasing accidentally.

In accordance with the present invention described above, it is possible to measure the maximal blood pressure in a short time without increasing the cuff pressure to a pressure which is substantially higher than the maximal blood pressure of the patient. Accordingly, it is possible to reduce the discomfort to the patient to a minimum.

In addition, the cuff pressure is rapidly increased to a predetermined level immediately below the predicted maximal blood pressure of the patient and is abruptly reduced to the predicted minimal blood pressure. It is therefore possible to reduce the time required from the beginning to the end of measurement of blood pressure and, hence, minimize the discomfort inflicted upon the patient.

Furthermore, even if the pressure in the cuff 102 rises to some excessive level due to an arbitrary cause, it will not exceed the preset limit value. Accordingly, this sphygmomanometer of the invention excels in safety as well.

What is claimed is:
1. An automatic sphygmomanometer, comprising:
pressure detecting means for detecting a cuff pressure;
first pressure-increasing means for increasing said cuff pressure at a high pressure-increasing rate;
pulse-wave signal detecting means for detecting the amplitude of a pulse-wave signal of a subject while said first pressure-increasing means is increasing said cuff pressure;
predicting means for predicting predicted maximal and minimal blood pressures from the amplitude of said pulse-wave signal;
first determining means for determining whether said cuff pressure has increased to a predetermined level below said predicted maximal blood pressure;
second pressure-increasing means for increasing said cuff pressure at a low pressure-increasing rate slower than said high pressure-increasing rate of said first pressure-increasing means when said first determining means has determined that said cuff pressure is at least as high as the predetermined level below said predicted maximal blood pressure;

maximal blood pressure measuring means for measuring a measured maximal blood pressure while said second pressure-increasing means is increasing said cuff pressure;

first pressure-reducing means for reducing said cuff pressure at a high pressure-reducing rate immediately after said measured maximal blood pressure has been measured;

second determining means for determining whether said cuff pressure has decreased to a predetermined level above said predicted minimal blood pressure;

second pressure-reducing means for reducing said cuff pressure at a low pressure-reducing rate slower than said high pressure-reducing rate of said first pressure-reducing means after said second determining means has determined that said cuff pressure is at least as low as a predetermined level above said predicted minimal blood pressure; and minimal blood pressure measuring means for measuring a measured minimal blood pressure while said second pressure-reducing means is reducing said cuff pressure.

2. An automatic sphygmomanometer according to claim 1, including means for energizing said first pressure-increasing means after said cuff pressure has reached approximately 20 mmHg, said cuff pressure being rapidly increased until said cuff pressure reaches approximately 20 mmHg.

3. An automatic sphygmomanometer according to claim 1, wherein said high pressure-increasing rate of said first pressure-increasing means is approximately 50 mmHg/7 seconds.

4. An automatic sphygmomanometer according to claim 1, wherein said predicting means predicts said predicted maximal and minimal blood pressure by utilizing a proportion of the amplitude of said pulse-wave signal to the maximum amplitude thereof.

5. An automatic sphygmomanometer according to claim 1, wherein said predetermined level below said predicted maximal blood pressure is a pressure corresponding to the maximum amplitude of said pulse-wave signal.

6. An automatic sphygmomanometer according to claim 1, wherein the low pressure-increasing rate of said second pressure-increasing means is approximately 50 mmHg/12 seconds.

7. An automatic sphygmomanometer according to claim 1, wherein said first pressure-reducing means is energized by opening an exhaust valve.

8. An automatic sphygmomanometer according to claim 1, said predetermined level above said predicted minimal blood pressure is equal to approximately 10 mmHg plus a pressure corresponding to the maximum amplitude of said pulse-wave signal.

9. An automatic sphygmomanometer according to claim 8, wherein said pressure reducing rate of said second pressure-reducing means is approximately 50 mmHg/12 seconds.

10. An automatic sphygmomanometer according to claim 8, further comprising means for rapidly exhausting cuff charged air after said measuring means has measured said minimal blood pressure.

11. An automatic sphygmomanometer according to claim 8 further including a limiter means for preventing said cuff pressure from exceeding a predetermined pressure.

12. A method for automatically measuring blood pressure, comprising the steps of:
  (a) detecting a cuff pressure;
  (b) increasing the cuff pressure at a first pressure-increasing rate;
  (c) detecting the amplitude of a pulse-wave signal of a subject while the cuff pressure is increasing at the first pressure-increasing rate in step (b);
  (d) predicting a predicted maximal blood pressure from the amplitude of the pulse-wave;
  (e) determining whether the cuff pressure has increased to a predetermined level below the predicted maximal blood pressure;
  (f) increasing the cuff pressure at a second pressure-increasing rate slower than the first pressure-increasing rate after said determining in step (e);
  (g) measuring a measured maximal blood pressure while the cuff pressure is increasing at the second pressure-increasing rate in step (f); and
  (h) ending said increasing in step (f) after said measuring in step (g) of the measured maximum blood pressure has been completed.

13. A method as recited in claim 12, further comprising the steps of:
  (i) reducing the cuff pressure at a first pressure-reducing rate immediately after said ending in step (h);
  (j) predicting a minimal blood pressure from the amplitude of the pulse-wave signal;
  (k) determining whether the cuff pressure has decreased to a second predetermined level above the predicted minimal blood pressure;
  (l) reducing the pressure at a second pressure-reducing rate slower than the first pressure-reducing rate after said determining in step (k) has determined that the cuff pressure has reached the second predetermined level above the predicted minimal blood pressure; and
  (m) measuring a measured minimal blood pressure during said decreasing in step (l).

* * * * *

UNITED STATES PATENT AND TRADEMARK OFFICE
CERTIFICATE OF CORRECTION

PATENT NO. : 5,197,478
DATED : March 30, 1993
INVENTOR(S) : Souma

It is certified that error appears in the above-identified patent and that said Letters Patent is hereby corrected as shown below:

Title page, item [63], after abandoned, insert, —filed as PCT/JP87/00899, Nov. 19, 1987—

Col. 3, lines 6-7, 12-13, 51 and 52, "pressure reducing" should be --pressure-reducing--;

Col. 5, line 53, "pressure-increase" should be --pressure increase--.

Col. 6, lines 29 and 32, "pressure-increase" should be --pressure increase--;

line 64, after "its" insert --maximum amplitude while the pressure in the cuff 102 is--.

Col. 9, line 54, after "1," insert --wherein--.
Col. 10, lines 4, 8 and 12, "8," should be --1,--.

Signed and Sealed this

Twenty-fifth Day of April, 1995

Attest:

BRUCE LEHMAN

Attesting Officer    Commissioner of Patents and Trademarks